(12) United States Patent
Aomatsu

(10) Patent No.: US 8,623,407 B2
(45) Date of Patent: *Jan. 7, 2014

(54) GABAPENTIN-CONTAINING SOLID COMPOSITIONS AND PROCESS FOR PREPARING THE SAME

(75) Inventor: Akira Aomatsu, Hachioji (JP)

(73) Assignee: Pfizer Inc., New York, NY (US)

(*) Notice: Subject to any disclaimer, the term of this patent is extended or adjusted under 35 U.S.C. 154(b) by 702 days.

This patent is subject to a terminal disclaimer.

(21) Appl. No.: 12/273,692

(22) Filed: Nov. 19, 2008

(65) Prior Publication Data

US 2009/0156677 A1 Jun. 18, 2009

Related U.S. Application Data

(63) Continuation of application No. 09/674,819, filed as application No. PCT/US99/10186 on May 10, 1999, now abandoned.

(30) Foreign Application Priority Data

May 15, 1998 (JP) ..................................... 98-133112

(51) Int. Cl.
*A61K 9/20* (2006.01)

(52) U.S. Cl.
USPC ........................................................ 424/464

(58) Field of Classification Search
USPC ........................................................ 424/464
See application file for complete search history.

(56) References Cited

U.S. PATENT DOCUMENTS

| 4,024,175 | A | | 5/1977 | Satzinger et al. | 260/468 |
|---|---|---|---|---|---|
| 4,087,544 | A | | 5/1978 | Satzinger et al. | 424/305 |
| 4,126,684 | A | | 11/1978 | Robson et al. | 424/254 |
| 4,486,412 | A | * | 12/1984 | Shah et al. | 424/601 |
| 4,952,560 | A | | 8/1990 | Kigasawa et al. | 514/2 |
| 5,025,035 | A | | 6/1991 | Wallace | 514/530 |
| 5,084,478 | A | | 1/1992 | Hughes et al. | 514/520 |
| 5,084,479 | A | | 1/1992 | Woodruff | 514/530 |
| 5,091,184 | A | | 2/1992 | Khanna | 424/435 |
| 5,503,845 | A | * | 4/1996 | Goede et al. | 424/464 |
| 5,510,381 | A | | 4/1996 | Pande | 514/561 |
| 6,054,482 | A | | 4/2000 | Augart et al. | 514/561 |

FOREIGN PATENT DOCUMENTS

| EP | 0458751 | 11/1991 | ............ A61K 31/195 |
|---|---|---|---|
| JP | 63253022 | 10/1988 | ............. A61K 31/95 |

OTHER PUBLICATIONS

Hoekstra (Chemical development of CI-1008, an Enantiomerically Pure Anticonvulsant, Organic Process Research and Development, pp. 26-38, 1997).*

* cited by examiner

*Primary Examiner* — Frederick Krass
*Assistant Examiner* — Adam C Milligan
(74) *Attorney, Agent, or Firm* — J. Michael Dixon

(57) ABSTRACT

The present invention provides a stabilized solid composition containing a 4-amino 3-substituted-butanoic acid derivative which can be obtained by incorporating a humectant as a stabilizer.

9 Claims, No Drawings

GABAPENTIN-CONTAINING SOLID COMPOSITIONS AND PROCESS FOR PREPARING THE SAME

FIELD OF THE INVENTION

This invention relates to a stabilized solid composition comprising a 4-amino-3-substituted-butanoic acid derivative and a process for the preparation of the same.

Also, this invention relates to a solid pharmaceutical preparation of the 4-amino-3-substituted-butanoic acid derivative comprising the stabilize solid composition and a process for the preparation of the same.

More particularly, the invention is concerned with a stabilized solid pharmaceutical preparation of the 4-amino-3-substituted-butanoic acid derivative, including gabapentin, pregabalin, baclofen, 3-aminomethyl-4-cyclohexyl-butanoic acid, 3-aminomethyl-5-cyclohexyl pentanoic acid, 3-aminomethyl-4-phenyl-butanoic acid or 3-aminomethyl-5-phenyl-pentanoic acid, in the dosage forms of tablets, powders, granules and capsules, as well as a process for the preparation of the same.

BACKGROUND OF THE INVENTION 1-(Aminomethyl)cyclohexaneacetic acid, one of the 4-amino-3-substituted-butanoic acid derivatives, having the following structural formula is disclosed in U.S. Pat. Nos. 4,024,175 and 4,087,544 and has been called "gabapentin", a generic name, due to its structural relation to γ-aminobutyric acid (GABA).

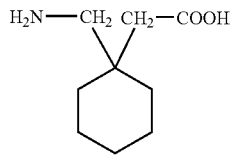 [SMILES: NCC1(CC(=O)O)CCCCC1]

Gabapentin easily passes across the brain barrier. Owing to this, the compound is used as a medicine for the treatment of certain cerebral diseases such as certain forms of epilepsy, faint and hypokinesia as well as cranial traumas, and also for improving the cerebral functions in senile patients.

Moreover, U.S. Pat. No. 5,084,479 discloses that gabapentin is used for the treatment of neurodegenerative disorders such as Alzheimer's disease, Huntington's chorea or Parkinson's disease and amyotrophic lateral sclerosis. U.S. Pat. No. 5,025,035 discloses that gabapentin is used for the treatment of depression. U.S. Pat. No. 5,510,381 discloses that this compound is used for the treatment of mania and bipolar disorder. Furthermore, this compound, having an analgesic activity, is expected to be used as analgesics. Under these circumstances, there has been a greatly increased utility of gabapentin as the therapeutic agents for those diseases or disorders or conditions as recited above, in addition to cerebral diseases such as epilepsy and the like.

As stated above, gabapentin is a very effective drug for cerebral diseases such as epilepsy and the like, and it has an extremely low toxicity. However, in order to maintain the effect as expected, it has been administered to adults usually at a single daily dose of 900-1800 mg or in some cases a daily dose of up to 2400 mg in three divided doses. Thus, a single dose will be in the range of 300-600 mg or in some cases up to 800 mg.

Further, gabapentin has difficulties in that it is a drug having a strongly bitter taste and also a very poor fluidity and that an extremely high dosage should be required for administration in the dosage form of powders. Since gabapentin is very difficult to formulate because of its instability, gabapentin capsules now available in the oversea markets are those manufactured by a simple dry blending of gabapentin with necessary auxiliaries and subsequent encapsulating into hard capsules.

However, a single dose is as high as 300-600 mg or in some cases up to 800 mg as stated above, which necessitates large-sized capsules; for example, Capsule No. 0 should be applied to capsules having a content of 400 mg per capsule. Consequently, ingesting such capsules is difficult even for adults, much more for children. Although gabapentin capsules have already been marketed, it is still indispensable to attempt any improvement in compliance and easy administration of gabapentin, and a demand for a smaller-sized pharmaceutical preparation of gabapentin exists in the clinical field.

Gabapentin itself is a powdery material having very poor compression-moldability and fluidity. Compression molding or granulation has been usually employed for small-sizing or fluidizing of the drug having such powder properties and the molding properties should be improved with the aid of pharmaceutical auxiliaries. However, many of the auxiliaries to be applied for compression molding tend to react with gabapentin with lapse of time to form 4-cyclohexylpyrrolidone (the corresponding lactam form) by accelerating the dehydration reaction between the amino group and the carboxyl group within the molecule of gabapentin. This dehydration reaction would be far more accelerated as the gabapentin powder is being more tightly compressed. Moreover, the reaction between gabapentin and such auxiliaries with lapse of time would be further accelerated by the use of water or an organic solvent in manufacturing a pharmaceutical preparation.

It has been standardized in commercially available gabapentin capsules that an allowable content of the lactam up to the beyond-use date should be no more than 1.0% in view of safety. Accordingly, it is necessary in manufacturing a pharmaceutical preparation of gabapentin to prevent the formation of the lactam by retarding the dehydration reaction between the amino group and the carboxyl group within the molecule of gabapentin. On the other hand, there has been a demand for a small-sized dosage form for easier ingesting as discussed above. Under such circumstances, there have been attempted over years various methods. However, none of these attempts has succeeded either because a large-sized dosage form resulted due to a large amount of the auxiliaries used or because an increased amount of the lactam formed or both of them.

Such instability as encountered in manufacturing a gabapentin preparation has been also observed in other 4-amino-3-substituted-butanoic acid derivatives which are structurally analogous to gabapentin and have a structurally bulky substituent at the 3-position thereof similarly to gabapentin.

For example, 4-amino-3-p-chlorophenyl)butanoic acid, which is represented by the following structural formula and called "baclofen" in a generic name,

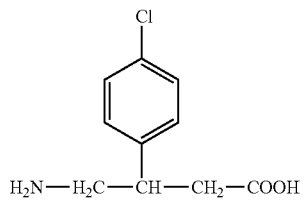

and 5-methyl-3-aminomethyl-hexanoic acid, which is represented by the following structural formula and called "pregabalin" in a generic name,

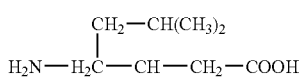

are also a drug which has very poor compression-moldability and fluidity like gabapentin. Compression molding or granulation used for small-sizing or fluidizing the drug should be improved with the aid of pharmaceutical auxiliaries. However, many of the auxiliaries to be applied to compression molding tend to react with gabapentin with lapse of time to form 4-cyclohexylpyrrolidone (the corresponding lactam form) by accelerating the dehydration reaction between the amino group and the carboxyl group within the molecule of the compound. This dehydration reaction would be far more accelerated as the compound is being more tightly compressed and would be further accelerated by the use of water or an organic solvent in manufacturing a pharmaceutical preparation, as is the case of gabapentin. It may be said that the mechanism of degradation by the autocondensation is peculiar to the 4-amino-3-substituted-butanoic acid derivatives having a structurally bulky substituent at the 3-position thereof.

To the contrary, in γ-aminobutyric acid derivatives having no or a less bulky substituent at the 3-position thereof, such as γ-aminobutyric acid or 4-amino-3-hydroxy-butanoic acid, the dehydration reaction is not brought about even when maintained in a dried state such as at a temperature of 105° C. over 2-3 hours, and the formation of 4-cyclohexylpyrrolidone (the corresponding lactam form) is not observed. In other words, in the 4-amino-3-substituted-butanoic acid derivative wherein the substituent at the 3-position thereof has a bulky structure, the dehydration reaction could easily be brought about between the amino group and the carboxyl group within the molecule.

In view of the aforesaid background, for drugs which are 4-amino-3-substituted-butanoic acid derivatives, including gabapentin, having a structurally bulky substituent at the 3-position thereof, there have been desired a new pharmaceutical preparation containing said drugs which may be small-sized or fluidized in a dosage form such as tablets or granules and may have a comparable storage stability to commercially available, pharmaceutical preparations including commercially available gabapentin capsules, and a process for manufacturing the same.

SUMMARY OF THE INVENTION

We have made earnest studies to solve the prior art problems as stated above and, as a result, have now found that the degradation of 4-amino-3-substituted-butanoic acid derivatives including gabapentin owing to the lactam formation during the formulation and storage can be prevented by blocking the evaporation and movement of a very small amount of residual water in a solid composition containing the 4-amino-3-substituted-butanoic acid derivative manufactured, irrespective of formulation methods employed, that it is effective to add a humectant as a stabilizer against degradation and that a solid composition containing the 4-amino-3-substituted-butanoic acid derivative stabilized by said humectant and a solid pharmaceutical preparation using said composition such as tablets, granules or the like have an excellent storage stability, on the basis of which this invention has been completed.

DETAILED DESCRIPTION OF THE INVENTION

The present invention relates to a stabilized solid composition containing a 4-amino-3-substituted-butanoic acid derivative which comprises a 4-amino-3-substituted-butanoic acid derivative having the general formula

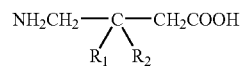

wherein, $R_1$ is a hydrogen atom, a hydroxyl group, a methyl group or an ethyl group;

$R_2$ is a monovalent group selected from:
a straight or branched alkyl group of 3-8 carbon atoms;
a straight or branched alkylene group of 3-8 carbon atoms;
a straight or branched alkyl group of 3-8 carbon atoms which is mono- or di-substituted with a halogen atom, a trifluoromethyl group, a hydroxyl group, an alkoxy group, an alkylthio group, an amino group, a nitro group, an oxo group, a carboxyl group or a carboalkoxy group;
a cycloalkyl group of 3-8 carbon atoms;
a cycloalkyl group of 3-8 carbon atoms which is mono-, di- or tri-substituted with a halogen atom, a trifluoromethyl group, a hydroxyl group, an alkyl group, an alkoxy group, an alkylthio group, an amino group, a nitro group, an oxo group, a carboxyl group or a carboalkoxy group;
a condensed ring group formed by ortho-fusion of a phenyl ring with a cycloalkyl group of 4-8 carbon atoms;
a condensed ring group formed by ortho-fusion of a phenyl ring with a cycloalkyl group of 4-8 carbon atoms wherein said phenyl ring is mono-, di- or tri-substituted with a halogen atom, a trifluoromethyl group, a hydroxyl group, an alkyl group, an alkoxy group, an alkylthio group, an amino group, a nitro group, a carboxyl group or a carboalkoxy group;
a condensed ring group formed by ortho-fusion of a phenyl ring with a cycloalkenyl group of 5-8 carbon atoms or a cycloalkanedienyl group of 5-8 carbon atoms;
a condensed ring group formed by ortho-fusion of a phenyl ring with a cycloakenyl group of 5-8 carbon atoms or a cycloalkanedienyl group of 5-8 carbon atoms wherein said phenyl ring is mono-, di- or tri-substituted with a halogen atom, a trifluoromethyl group, a hydroxyl group, an alkyl group, an alkoxy group, an alkylthio group, an amino group, a nitro group, a carboxyl group or a carboalkoxy group;
an alkylcycloalkyl group wherein said cycloalkyl has 3-8 carbon atoms and is linked to an alkylene group having 1-4 carbon atoms optionally interrupted with —O—, —S— or —SS—;
an alkylcycloalkyl group wherein said cycloalkyl has 3-8 carbon atoms, is linked to an alkylene group having 1-4 carbon atoms optionally interrupted with —O—, —S— or —SS— and is mono-, di- or tri-substituted with a halogen atom, a trifluoromethyl group, a hydroxyl group, an alkyl group, an alkoxy group, an alkylthio group, an amino group, a nitro group, an oxo group, a carboxyl group or a carboalkoxy group;
a cycloalkyl group of 5-8 carbon atoms wherein one of the methylene groups (—CH$_2$—) is replaced by —O—, —NH—, —S—, —SO— or —S(O)$_2$—;
a cycloalkyl group of 5-8 carbon atoms wherein one of the methylene groups (—CH$_2$—) is replaced by —O—, —NH—, —S—, —SO— or —S(O)$_2$—, and one or two of the unsubstituted methylene groups (—CH$_2$—) are mono- or di-substituted with a halogen atom, a trifluoromethyl group, a hydroxyl group, an alkyl group, an alkoxy group, an alkylthio group, an amino group, a nitro group, an oxo group, a carboxyl group or a carboalkoxy group;

a cycloalkenyl group of 5-8 carbon atoms or a cycloalkanedienyl group of 5-8 carbon atoms, one of the methylene groups (—CH$_2$—) in said cycloalkenyl ring or cycloalkanedienyl ring being replaced by —O—, —NH—, =N—, —S—, —SO— or —S(O)$_2$—;

a cycloalkenyl group of 5-8 carbon atoms or a cycloalkanedienyl group of 5-8 carbon atoms, one of the methylene groups (—CH$_2$—) in said cycloalkenyl ring or cycloalkanedienyl ring being replaced by —O—, —NH—, =N—, —S—, —SO— or —S(O)$_2$—, and one or two of the unsubstituted methylene groups (—CH$_2$—) being mono- or di-substituted with a halogen atom, a trifluoromethyl group, a hydroxyl group, an alkyl group, an alkoxy group, an alkylthio group, an amino group, a nitro group, an oxo group, a carboxyl group or a carboalkoxy group;

a condensed ring group formed by ortho-fusion of a phenyl ring with a cycloalkyl group of 5-8 carbon atoms wherein one of the methylene groups (—CH$_2$—) is replaced by —O—, —NH—, —S—, —SO— or —S(O)$_2$—;

a condensed ring group formed by ortho-fusion of a phenyl ring with a cycloalkyl group of 5-8 carbon atoms wherein one of the methylene groups (—CH$_2$—) is replaced by —O—, —NH—, —S—, —SO— or —S(O)$_2$—, said phenyl group being mono- or di-substituted with a halogen atom, a trifluoromethyl group, a hydroxyl group, an alkyl group, an alkoxy group, an alkylthio group, an amino group, a nitro group, a carboxyl group or a carboalkoxy group;

a condensed ring group formed by ortho-fusion of a phenyl ring with a cycloalkenyl group of 5-8 carbon atoms or a cycloalkanedienyl group of 5-8 carbon atoms, one of the methylene groups (—CH$_2$—) in said cycloalkenyl ring or cycloalkanedienyl ring being replaced by —O—, —NH—, =N—, —S—, —SO— or —S(O)$_2$—:

a condensed ring group formed by ortho-fusion of a phenyl ring with a cycloalkenyl group of 5-8 carbon atoms or a cycloalkanedienyl group of 5-8 carbon atoms, one of the methylene groups (—CH$_2$—) in said cycloalkenyl ring or cycloalkanedienyl ring being replaced by —O—, —NH—, =N—, —S—, —SO— or —S(O)$_2$—, said phenyl ring being mono- or di-substituted with a halogen atom, a trifluoromethyl group, a hydroxyl group, an alkyl group, an alkoxy group, an alkylthio group, an amino group, a nitro group, a carboxyl group or a carboalkoxy group;

an alkylcycloalkyl group wherein said cycloalkyl has 5-8 carbon atoms and is linked to an alkylene group having 1-4 carbon atoms optionally interrupted with —O—, —S— or —SS—, one of the methylene groups (—CH$_2$—) in said cycloalkyl ring being replaced by —O—, —NH—, —S—, —SO— or —S(O)$_2$—;

an alkylcycloalkyl group wherein said cycloalkyl has 5-8 carbon atoms and is linked to an alkylene group having 1-4 carbon atoms optionally interrupted with —O—, —S— or —SS—, and one of the methylene groups (—CH$_2$—) in said cycloalkyl ring being replaced by —O—, —NH—, —S—, —SO— or —S(O)$_2$— and one or two of the unsubstituted methylene groups (CH$_2$—) being mono-, di- or tri-substituted with a halogen atom, a trifluoromethyl group, a hydroxyl group, an alkyl group, an alkoxy group, an alkylthio group, an amino group, a nitro group, an oxo group, a carboxyl group or a carboalkoxy group;

a phenyl or naphthyl group;

a phenyl group substituted with a methylenedioxy group;

a phenyl or naphthyl group which is mono-, di- or tri-substituted with a halogen atom, a trifluoromethyl group, a hydroxyl group, an alkyl group, an alkoxy group, an amino group, a nitro group, a carboxyl group, a phenoxy group, a phenylmethoxy group, a phenylmethoxy group wherein said phenyl ring is mono-substituted with a halogen atom, trifluoromethyl group, an alkoxy group, an amino group, a nitro group, a carboxyl group or a carboalkoxy group, a cycloalkylmethoxy group having 5-8 carbon atoms in the cycloalkyl ring, a cycloalkenylmethoxy group having 5-8 carbon atoms in the cycloalkenyl ring, a cycloalkanedienylmethoxy group having 5-8 carbon atoms in the cycloalkanedienyl ring, a cycloalkylmethoxy group wherein one of the methylene groups (—CH$_2$—) in said cycloalkyl ring having 5-8 carbon atoms is replaced by —O—, —NH—, —S—, —SO— or —S(O)$_2$—, a cycloalkenylmethoxy group wherein one of the methylene groups (—CH$_2$—) in said cycloalkenyl ring having 5-8 carbon atoms is replaced by —O—, —NH—, =N—, —S—, —SO— or —S(O)$_2$—, a cycloalkanedienyl-methoxy group wherein one of the methylene groups (—CH$_2$—) in said cycloalkanedienyl ring having 5-8 carbon atoms is replaced by —O—, —NH—, =N—, —S—, —SO— or —S(O)$_2$— group, a cycloalkylmethoxy group having 5-8 carbon atoms in the cycloalkyl ring wherein said cycloalkyl ring is mono-substituted with a halogen atom, trifluoromethyl group, a hydroxy group, an alkyl group, an alkoxy group, an amino group, a nitro group, a carboxyl group or a carboalkoxy group and one of the methylene groups (—CH$_2$—) in said cycloalkyl ring is replaced by —O—, —NH—, —S—, —SO— or —S(O)$_2$—, a cycloalkenylmethoxy group having 5-8 carbon atoms in the cycloalkenyl ring wherein said cycloalkenyl ring is mono-substituted with a halogen atom, a trifluoromethyl group, a hydroxy group, an alkyl group, an alkoxy group, an amino group, a nitro group, an oxo group, a carboxyl group or a carboalkoxy group and one of the methylene groups (—CH$_2$—) in said cycloalkenyl ring is replaced by —O—, —NH—, =N—, —S—, —SO— or —S(O)$_2$—, or a cycloalkanedienylmethoxy group having 5-8 carbon atoms in the cycloalkanedienyl ring wherein said cycloalkanedienyl ring is mono-substituted with a halogen atom, a trifluoromethyl group, a hydroxyl group, an alkyl group, an alkoxy group, an amino group, a nitro group, an oxo group, a carboxyl group or a carboalkoxy group and one of the methylene groups (—CH$_2$—) in said cycloalkanedienyl ring is replaced by —O—, —NH—, =N—, —S—, —SO— or —S(O)$_2$—;

an alkylphenyl group wherein said phenyl group is linked to an alkylene group having 1-4 carbon atoms optionally interrupted with —O—, —S— or —SS—;

an alkyl-O—, —S— or —SS-phenyl group wherein said phenyl group is linked to an alkylene group having 1-4 carbon atoms via —O—, —S— or —SS:

an —O—, —S— or —SS-phenyl group:

a diphenylamino group;

an alkylphenyl group wherein said phenyl group is linked to an alkylene group having 1-4 carbon atoms optionally interrupted with —O—, —S— or —SS— and mono-, di- or tri-substituted with a halogen atom, a trifluoromethyl group, a hydroxyl group, a alkyl group, an alkoxy group, an amino group, a nitro group or a carboxyl group;
an alkyl-O—, —S— or —SS-phenyl group wherein said phenyl group is linked to an alkylene group having 1-4 carbon atoms via —O—, —S— or —SS— and mono-, di- or tri-substituted with a halogen atom, a trifluoromethyl group, a hydroxyl group, an alkyl group, an alkoxy group, an amino group, a nitro group or a carboxyl group;
an —O—, —S— or —SS-phenyl group wherein said phenyl group is mono-, di- or tri-substituted with a halogen atom, a trifluoromethyl group, a hydroxyl group, an alkyl group, an alkoxy group, an amino group, a nitro group or a carboxyl group;
or
$R_1$ and $R_2$, together with the carbon atom to which they are attached, may form a divalent group selected from:
a cycloalkylidene group of 5-8 carbon atoms;
a cycloalkylidene group of 5-8 carbon atoms which is mono-, di-, tri- or tetra-substituted with a halogen atom, a trifluoromethyl group, a hydroxyl group, an alkyl group, an alkoxy group, an alkylthio group, a cycloalkyl group, a phenyl group, an amino group, a nitro group or a carboxyl group;
a cycloalkylidene group of 5-8 carbon atoms wherein one of the methylene groups (—$CH_2$—) in said cycloalkyl ring is replaced by —O—, —NH—, —S—, —O— or —$S(O)_2$—;
a cycloalkylidene group of 5-8 carbon atoms wherein one of the methylene groups (—$CH_2$—) in said cycloalkyl ring is replaced by —O—, —NH—, —S—, —SO— or —$S(O)_2$— group and one or more of the unsubstituted methylene groups (—$CH_2$—) in said cycloalkyl ring are mono-, di-, tri- or tetra-substituted with a halogen atom, a trifluoromethyl group, a hydroxyl group, an alkyl group, an alkoxy group, an alkylthio group, an amino group, a nitro group, an oxo group, a carboxyl group or a carboalkoxy group;
a cycloalkenylidene group of 5-8 carbon atoms or a cycloalkanedienylidene group of 5-8 carbon atoms;
a cycloalkenylidene group of 5-8 carbon atoms or a cycloalkanedienylidene group of 5-8 carbon atoms which is mono-, di-, tri- or tetra-substituted with a halogen atom, a trifluoromethyl group, a hydroxyl group, an alkyl group, an alkoxy group, an alkylthio group, a cycloalkyl group, a phenyl group, an amino group, a nitro group, an oxo group, a carboxyl group or a carboalkoxy group;
a cycloalkenylidene group of 5-8 carbon atoms or a cycloalkanedienylidene group of 5-8 carbon atoms wherein one of the methylene groups (—$CH_2$—) in said cycloalkenyl ring or cycloalkanedienyl ring is replaced by —O—, —NH—, =N—, —S—, —SO— or —$S(O)_2$—;
a cycloalkenylidene group of 5-8 carbon atoms or a cycloalkanedienylidene group of 5-8 carbon atoms wherein one of the methylene groups (—$CH_2$—) in said cycloalkenyl ring or cycloalkanedienyl ring is replaced by —O—, —NH—, =N—, —S—, —SO— or —$S(O)_2$— group and one or more of the unsubstituted methylene groups (—$CH_2$—) in said cycloalkenyl ring or cycloalkanedienyl ring are mono-, di-, tri- or tetra-substituted with a halogen atom, a trifluoromethyl group, a hydroxyl group, an alkyl group, an alkoxy group, an alkylthio group, an amino group, a nitro group, an oxo group, a carboxyl group or a carboalkoxy group;

a condensed ring group formed by ortho-fusion of a phenyl ring with a cycloalkylidene group of 4-8 carbon atoms;
a condensed ring group formed by ortho-fusion of a phenyl ring with a cycloalkylidene group of 4-8 carbon atoms, said phenyl ring being mono-, di-, tri- or tetra-substituted with a halogen atom, a trifluoromethyl group, a hydroxyl group, an alkyl group, an alkoxy group, an alkylthio group, an amino group, a nitro group, a carboxyl group or a carboalkoxy group;
a condensed ring group formed by ortho-fusion of a phenyl ring with a cycloalkenylidene group of 5-8 carbon atoms or a cycloalkanedienylidene group of 5-8 carbon atoms;
a condensed ring group formed by ortho-fusion of a phenyl ring with a cycloalkenylidene group of 5-8 carbon atoms or a cycloalkanedienylidene group of 5-8 carbon atoms, said phenyl ring being mono- or di-substituted with a halogen atom, a trifluoromethyl group, a hydroxyl group, an alkyl group, an alkoxy group, an alkylthio group, an amino group, a nitro group, a carboxyl group or a carboalkoxy group;
a humectant; and, if necessary, an auxiliary agent for manufacturing a pharmaceutical preparation.

The invention also relates to a solid composition containing a 4-amino-3-substituted-butanoic acid derivative which is a solid pharmaceutical preparation in the dosage form of tablets, powders, granules or capsules.

Also, the invention relates to a process for the preparation of a solid composition containing a 4-amino-3-substituted-butanoic acid derivative which comprises combining a 4-amino-3-substituted-butanoic acid derivative having the following formula

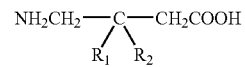

(wherein $R_1$ and $R_2$ are as defined above) with a humectant and, if necessary, an auxiliary agent for manufacturing a pharmaceutical preparation.

The invention further relates to a process for the preparation of a solid composition containing a 4-amino-3-substituted-butanoic acid derivative which is a solid pharmaceutical preparation in the dosage form of tablets, powders, granules or capsules.

The invention furthermore relates to a stabilized solid composition containing a 4-amino-3-substituted-butanoic acid derivative which further comprises a neutral amino acid.

The 4-amino-3-substituted-butanoic acid derivatives which may be stabilized according to the present invention include those compounds as listed in the following Tables 1 and 2:

TABLE 1

$$NH_2CH_2-\underset{R_1\ R_2}{C}-CH_2COOH$$

| —$R_1$ | —$R_2$ |
|---|---|
| —H | —$CH_2$—$CH_2$—$CH_3$ |
| —H | —$CH(CH_3)_2$ |
| —H | —$CH_2$—$CH_2$—$CH_2$—$CH_3$ |
| —H | —$CH_2$—$CH(CH_3)_2$ |
| —H | —$C(CH_2)_3$ |
| —H | —$(CH_2)_4$—$CH3$ |
| —H | —$(CH_2)_3$—$CH$—$(CH_3)_2$ |
| —H | —$CH(CH_2$—$CH_3)(CH_3)$ |

TABLE 1-continued $$NH_2CH_2-\underset{\underset{R_2}{|}}{\overset{\overset{R_1}{|}}{C}}-CH_2COOH$$

| —$R_1$ | —$R_2$ |
|---|---|
| —H | —CH$_2$—CH$_2$—CH$_2$NH$_2$ |
| —H | —CH$_2$—CH$_2$—CH$_2$—CH$_2$—NH$_2$ |
| —H | —CH$_2$—CH$_2$—CH$_2$Cl |
| —H | —CH$_2$—CH$_2$—CH$_2$OH |
| —H | 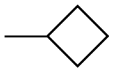 |
| —H | 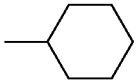 |
| —H | 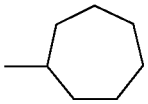 |
| —H | 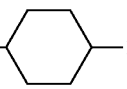 |
| —H | 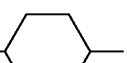 |
| —H | 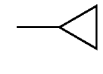 |
| —H | —CH$_2$—CH$_2$—CH$_2$—CH$_2$—Cl |
| —H | —CH$_2$—CH$_2$—CH$_2$Br |
| —H | —CH$_2$—CH$_2$—CH$_2$I |
| —H | —CH$_2$—CH(CH$_3$)—CHCl |
| —H | —CH$_2$—CO—CH$_3$ |
| —H | —CH$_2$—CH$_2$—CO—CH$_3$ |
| —H | —CH$_2$—CH$_2$—CH$_2$—CHOH |
| —H | 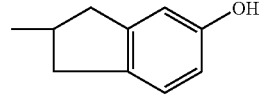 |
| —H | 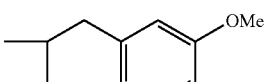 |
| —H | 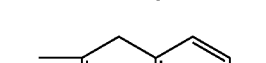 |
| —H |  |
| —H | 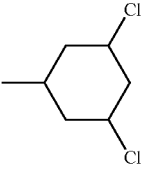 |

TABLE 1-continued $$NH_2CH_2-\underset{\underset{R_2}{|}}{\overset{\overset{R_1}{|}}{C}}-CH_2COOH$$

| —$R_1$ | —$R_2$ |
|---|---|
| —H | 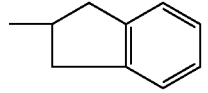 |
| —H | 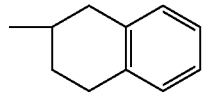 |
| —H | 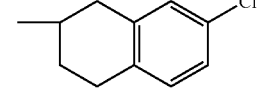 |
| —H | 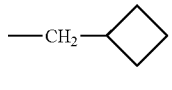 |
| —H | 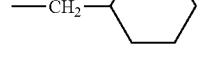 |
| —H | 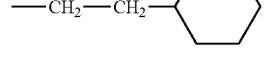 |
| —H | 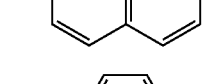 |
| —H | 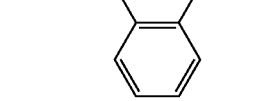 |
| —H | 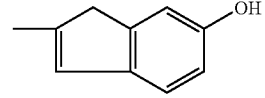 |
| —H | 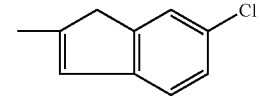 |
| —H | 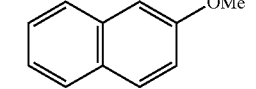 |
| —H | 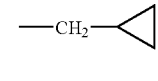 |

TABLE 1-continued $$NH_2CH_2-\underset{\underset{R_2}{R_1}}{C}-CH_2COOH$$

| −R₁ | −R₂ |
|---|---|
| −H | 2-pyrrolidinyl |
| −H | 2-imidazolidinyl |
| −H | 2-piperidinyl |
| −H | −CH₂−O−CH₂−cyclohexyl |
| −H | −CH₂−(4-hydroxycyclohexyl) |
| −H | −CH₂−(3-hydroxycyclohexyl) |
| −H | −CH₂−(4-methoxycyclohexyl) |
| −H | −CH₂−(4-chlorocyclohexyl) |
| −H | −CH₂−O−CH₂−(4-hydroxycyclohexyl) |
| −H | 2-tetrahydrofuranyl |
| −H | 5-hydroxy-2-piperazinyl |
| −H | 3-thienyl (dihydro) |
| −H | 2-furyl |
| −H | 5-methyl-2-piperazinyl |
| −H | 2-(1,4-dioxanyl) |
| −H | 4-hydroxy-2-pyrrolidinyl |
| −H | 3-hydroxy-2-piperidinyl |
| −H | 5-hydroxy-2-piperidinyl |
| −H | 5-methoxy-2-furyl |
| −H | 5-methyl-2-thienyl |
| −H | 2,3-dimethyl-5-thienyl |
| −H | 2-thienyl |
| −H | 2-imidazolyl |
| −H | 2-pyridyl |
| −H | 2-(1,4-dioxinyl) |

TABLE 1-continued
NH₂CH₂—C(R₁)(R₂)—CH₂COOH
| —R₁ | —R₂ |
|---|---|
| —H | 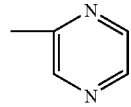 |
| —H | 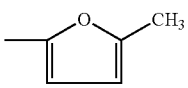 |
| —H | 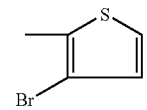 |
| —H | 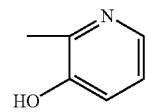 |
| —H | 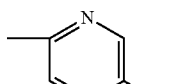 |
| —H | 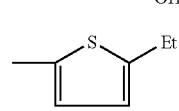 |
| —H | 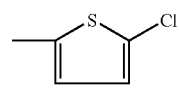 |
| —H | 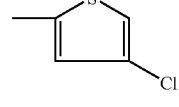 |
| —H | 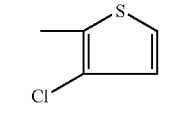 |
| —H | 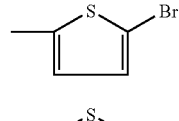 |
| —H | 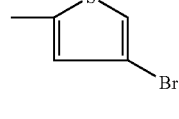 |
| —H | 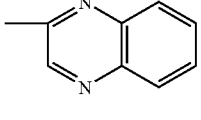 |
| —H | 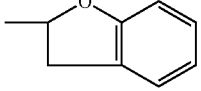 |
| —H | 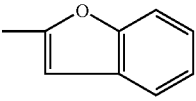 |
| —H | 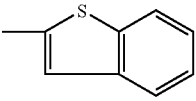 |
| —H | 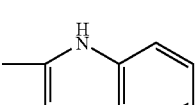 |
| —H | 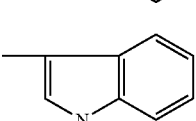 |
| —H | 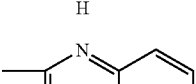 |
| —H | 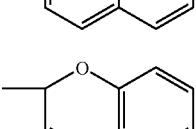 |
| —H | 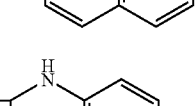 |
| —H | 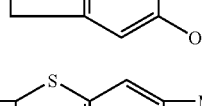 |
| —H | 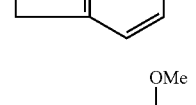 |
| —H | 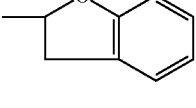 |
| —H | 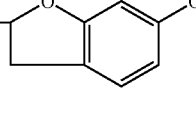 |
| —H | 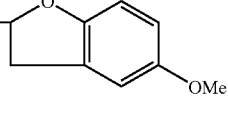 |

TABLE 1-continued
NH₂CH₂—C(R₁)(R₂)—CH₂COOH
| —R₁ | —R₂ |
|---|---|
| —H | 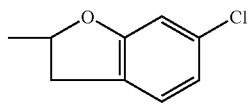 |
| —H | 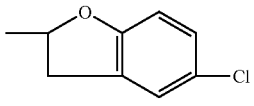 |
| —H | 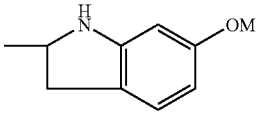 |
| —H | 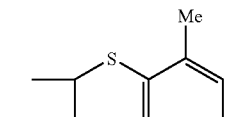 |
| —H | 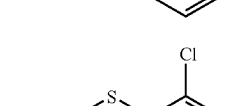 |
| —H | 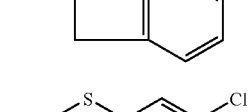 |
| —H | 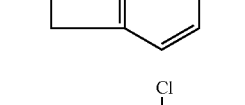 |
| —H | 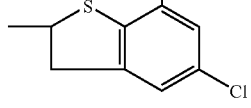 |
| —H | 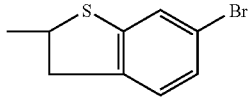 |
| —H | 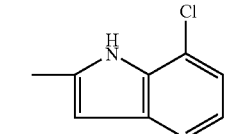 |
| —H | 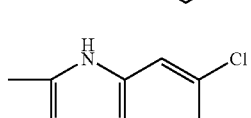 |
| —H | 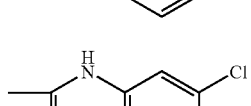 |
| —H | 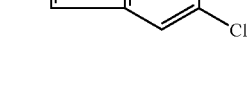 |
| —H | 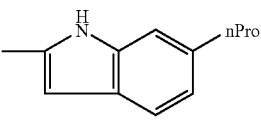 |
| —H | 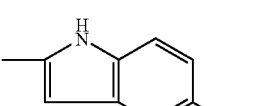 |
| —H |  |
| —H | 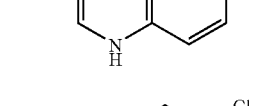 |
| —H | 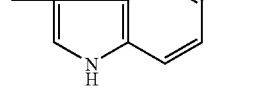 |
| —H | 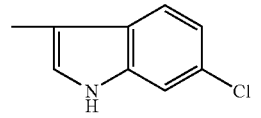 |
| —H | 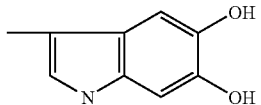 |
| —H | 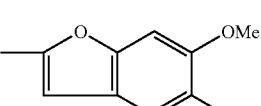 |
| —H | 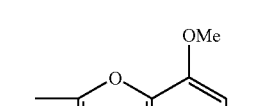 |
| —H | 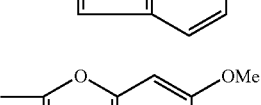 |
| —H | 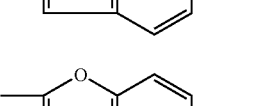 |
| —H | 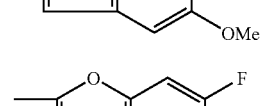 |
| —H | 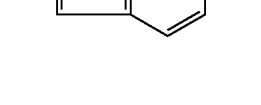 |

TABLE 1-continued $$NH_2CH_2-\underset{\underset{R_2}{|}}{\overset{\overset{R_1}{|}}{C}}-CH_2COOH$$

| —$R_1$ | —$R_2$ |
|---|---|
| —H | 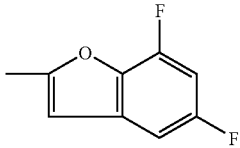 (2-methylbenzofuran with F at 4 and 7 positions) |
| —H | 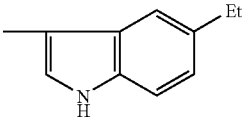 (5-ethylindole) |
| —H | 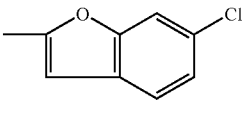 (2-methyl-6-chlorobenzofuran) |
| —H | 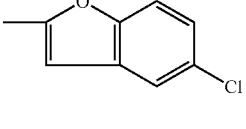 (2-methyl-5-chlorobenzofuran) |
| —H | 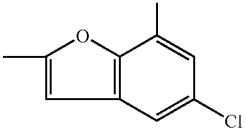 (2-methylbenzofuran with Cl at 5 and 7) |
| —H | 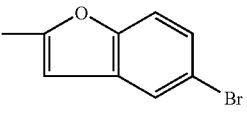 (2-methyl-5-bromobenzofuran) |
| —H | 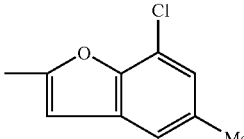 (2-methyl-7-Cl-5-Me-benzofuran) |
| —H | 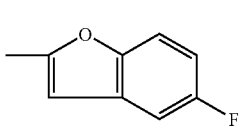 (2-methyl-5-fluorobenzofuran) |
| —H |  (2-methyl-7-chlorobenzofuran) |
| —H | 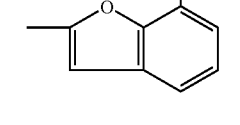 (2-methyl-7-ethylbenzofuran) |

TABLE 1-continued $$NH_2CH_2-\underset{\underset{R_2}{|}}{\overset{\overset{R_1}{|}}{C}}-CH_2COOH$$

| —$R_1$ | —$R_2$ |
|---|---|
| —H | 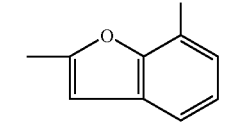 (2-methyl-6-ethylbenzofuran) |
| —H | 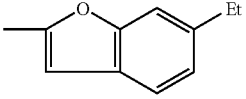 (2-methyl-5-ethylbenzofuran) |
| —H | 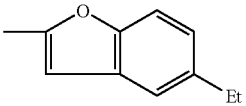 (2-methyl-7-nPro-benzofuran) |
| —H | 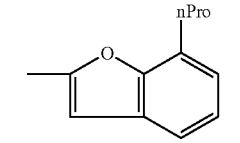 (2-methyl-5-nPro-benzofuran) |
| —H | 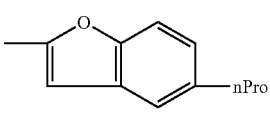 (2-methyl-7-Me-5-Cl-benzofuran) |
| —H | 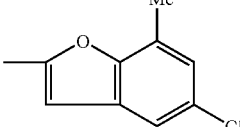 (2-methyl-7-methylbenzofuran) |
| —H | 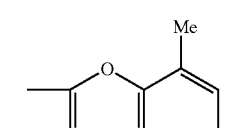 (2-methyl-6-methylbenzofuran) |
| —H | 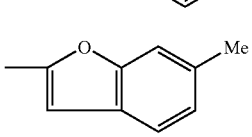 (2-methyl-5,6-dimethylbenzofuran) |
| —H | 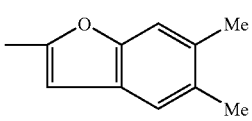 (2-methyl-7-ethoxybenzofuran) |
| —H | 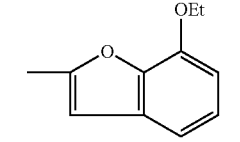 (2-methyl-5-ethoxybenzofuran) |
| —H | 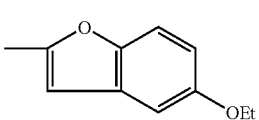 (2-methyl-7-isopropylbenzofuran) |

TABLE 1-continued
$$NH_2CH_2-\underset{\underset{R_2}{|}}{\overset{\overset{R_1}{|}}{C}}-CH_2COOH$$
| —R$_1$ | —R$_2$ |
|---|---|
| —H | 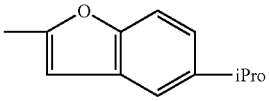 |
| —H | 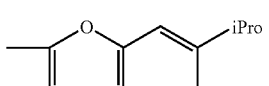 |
| —H | 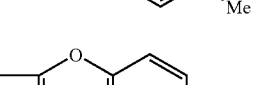 |
| —H | 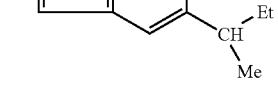 |
| —H | 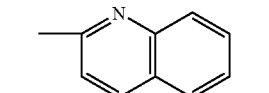 |
| —H |  |
| —H | 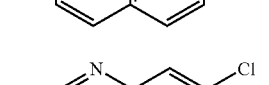 |
| —H | 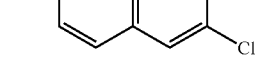 |
| —H | 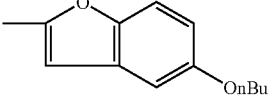 |
| —H | 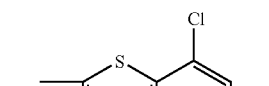 |
| —H | 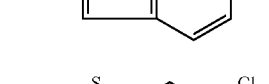 |
| —H | 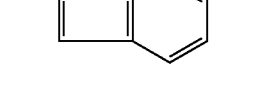 |
| —H | 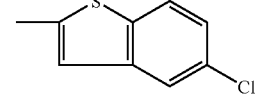 |
| —H | 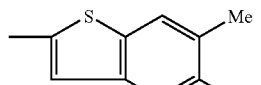 |
| —H | 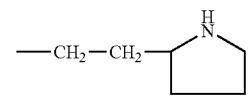 |
| —H | 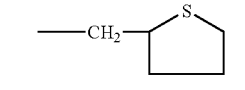 |
| —H | 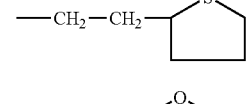 |
| —H | 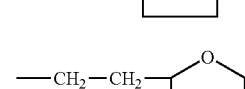 |
| —H | 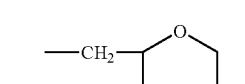 |
| —H | 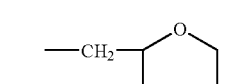 |
| —H | 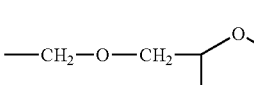 |
| —H | 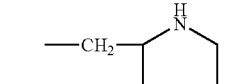 |
| —H | 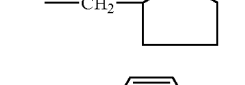 |
| —H | 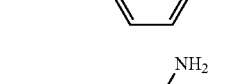 |
| —H | 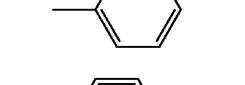 |
| —H | 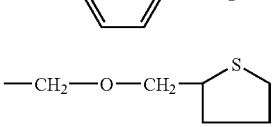 |

TABLE 1-continued
$$NH_2CH_2-\underset{\underset{R_2}{|}}{\overset{\overset{R_1}{|}}{C}}-CH_2COOH$$
| —R₁ | —R₂ |
|---|---|
| —H | 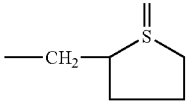 |
| —H | 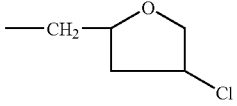 |
| —H | 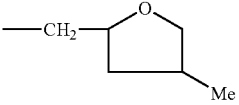 |
| —H | 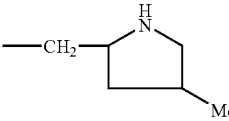 |
| —H | 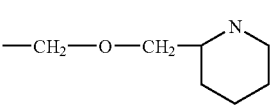 |
| —H | 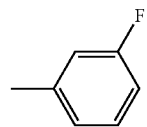 |
| —H | 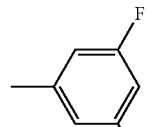 |
| —H | 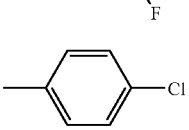 |
| —H | 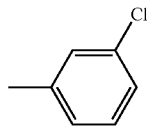 |
| —H | 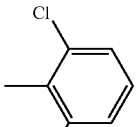 |
TABLE 1-continued
$$NH_2CH_2-\underset{\underset{R_2}{|}}{\overset{\overset{R_1}{|}}{C}}-CH_2COOH$$
| —R₁ | —R₂ |
|---|---|
| —H | 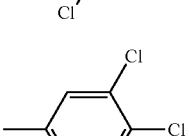 |
| —H | 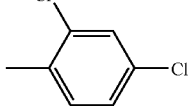 |
| —H | 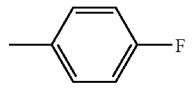 |
| —H | 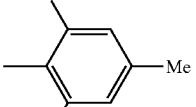 |
| —H | 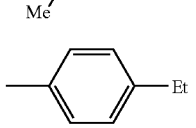 |
| —H | 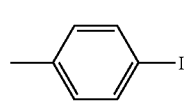 |
| —H | 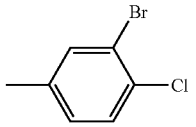 |
| —H | 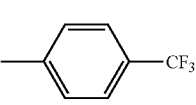 |
| —H | 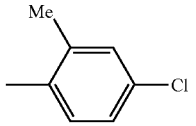 |
| —H | 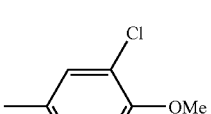 |
| —H | 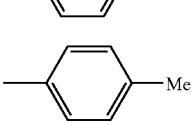 |
| —H | 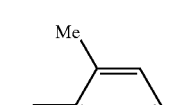 |
| —H | 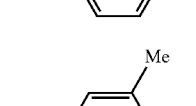 |

TABLE 1-continued $$NH_2CH_2-\underset{\underset{R_2}{|}}{\overset{\overset{R_1}{|}}{C}}-CH_2COOH$$

| —$R_1$ | —$R_2$ |
|---|---|
| —H | 4-nPro-phenyl |
| —H | 4-iPro-phenyl |
| —H | 4-OMe-phenyl |
| —H | 2,4-di-OMe-phenyl |
| —H | 4-OMe-3-Me-phenyl (4-methoxy, with Me at other position) |
| —H | 4-OH-phenyl |
| —H | 3-OH-phenyl |
| —H | 2-OH-phenyl |
| —H | 2-OMe-4-OH-phenyl |
| —H | 3-OMe-phenyl |
| —H | 2-OMe-phenyl |
| —H | 4-OMe-phenyl |
| —H | 2,3,4-tri-OMe-phenyl |
| —H | 4-OiPro-phenyl |
| —H | 3,4-di-OMe-phenyl |
| —H | 2,3,6-tri-OMe-phenyl (with Me) |
| —H | benzo[1,3]dioxol-5-yl |
| —H | 3-phenoxy-phenyl |
| —H | 4-phenoxy-phenyl |
| —H | 4-(benzyloxy)-phenyl |
| —H | 4-((5-chlorothiophen-2-yl)methoxy)phenyl |
| —H | —CH$_2$—O—CH$_2$-phenyl |
| —H | —CH$_2$—CH$_2$—S—CH$_2$-phenyl |

TABLE 1-continued $$NH_2CH_2-\underset{\underset{R_2}{|}}{\overset{\overset{R_1}{|}}{C}}-CH_2COOH$$

| —R₁ | —R₂ |
|---|---|
| —H | —CH₂—C₆H₅ |
| —H | 4-methyl-2-methoxy-1-(OtBu)phenyl (—C₆H₃(OMe)(OtBu)) |
| —H | 4-methyl-benzo[1,3]dioxole |
| —H | —CH₂—NH—C₆H₅ |
| —H | —N(C₆H₅)₂ |
| —H | —CH₂—O—CH₂—C₆H₃(3,4-Cl₂) |
| —H | —CH₂—S—CH₂—C₆H₃(3,4-Cl₂) |
| —H | —CH₂—S—CH₂—C₆H₄(4-Me) |
| —H | —CH₂—S—CH₂—CH₂—C₆H₃(2,4-Cl₂) |
| —H | —CH₂—S—CH₂—CH₂—C₆H₄(4-Cl) |
| —H | —CH₂—CH₂—C₆H₅ |
| —H | —CH₂—S—C₆H₅ |
| —H | —CH₂—O—C₆H₄(4-tBu) |
| —H | —CH₂—S—C₆H₄(4-Br) |
| —H | —CH₂—CH₂—S—C₆H₄(4-CF₃) |
| —H | —O—C₆H₄(4-Cl) |
| —H | —O—C₆H₄(4-CF₃) |
| —H | —SS—C₆H₄(4-Cl) |
| —H | —S—C₆H₃(3,4-Cl₂) |
| —H | —CH₂—CH₂—O—CH₂—C₆H₄(4-NH₂) |
| —H | —CH₂—CH₂—S—CH₂—C₆H₃(3,4-Cl₂) |
| —H | —CH₂—CH₂—S—CH₂—C₆H₄(4-Br) |
| —OH | —CH₂—C(CH₃)₃ |
| —OH | —CH₂—CH₂—CH₃ |
| —OH | —CH₂—CH₂—CH₂—CH₃ |
| —OH | —CH₂—CH(CH₃)₂ |
| —OH | —C₆H₅ |
| —OH | —C₆H₄(4-Cl) |

TABLE 1-continued $$NH_2CH_2-\underset{\underset{R_1}{|}\phantom{XX}\underset{R_2}{|}}{C}-CH_2COOH$$

| —R₁ | —R₂ |
|---|---|
| —OH | 3-chlorophenyl |
| —OH | 4-methylphenyl |
| —OH | —CH₂—O—phenyl |
| —H | —S—(4-chlorophenyl) |
| —H | 1-methyl-4-amino-pyrimidin-2(1H)-one (cytosine-N1-yl) |
| —H | 3-methyl-hexahydrobenzoxazol-2-one-6-yl |
| —CH₃ | —CH(CH₃)₂ |
| —CH₃ | —CH₂—CH(CH₃)₂ |
| —CH₃ | —CH₂—CH₂—CH₂—CH₃ |
| —CH₃ | phenyl |
| —CH₃ | 4-chlorophenyl |
| —CH₃ | —CH₂-phenyl |
| —CH₃ | —CH₂-cyclohexyl |
| —CH₂—CH₃ | —CH₂—CH(CH₃)₂ |
| —CH₃ | phenyl |
| —OH | cyclohexyl |

TABLE 1-continued $$NH_2CH_2-\underset{\underset{R_1}{|}\phantom{XX}\underset{R_2}{|}}{C}-CH_2COOH$$

| —R₁ | —R₂ |
|---|---|
| —OH | 4-chlorocyclohexyl |
| —OH | pyrrolidin-2-yl |
| —OH | tetrahydrofuran-2-yl |
| —OH | furan-2-yl |
| —OH | pyridin-2-yl |
| —CH₃ | —CH₂—CH₂—CH₃ |
| —H | —CH=CH—CH₃ |
| —H | —CH=CH—CH₂—CH₃ |
| —H | —C(CH₃)=CH—CH₃ |
| —H | —CH=C(CH₃)₂ |
| —CH₂—CH₃ | —CH₂-phenyl |
| —CH₂—CH₃ | 4-chlorophenyl |
| —CH₂—CH₃ | —CH₂-(4-chlorophenyl) |
| —CH₂—CH₃ | tetrahydrofuran-2-yl |
| —CH₂—CH₃ | furan-2-yl |
| —CH₂—CH₃ | pyridin-2-yl |
| —H | —CH=CH₂—CH₂—CH₃ |
| —H | —CH=CH—CH(CH₃)₂ |

TABLE 2

$$NH_2CH_2-\underset{\underset{R_2}{|}}{\overset{\overset{R_1}{|}}{C}}-CH_2COOH$$

(Table contains chemical structure drawings of various substituted cyclopentane, cyclohexane, and cycloheptane groups representing the R₁/R₂ substituent pair, including: gem-dimethyl cyclopentyl, gem-dimethyl cyclohexyl, gem-dimethyl cycloheptyl, and variously substituted derivatives bearing SMe, cyclohexyl, phenyl, Cl, NH₂, Br, COOH, di-Cl, di-Br, CF₃, OH, Me, =O, ketone, iPro, Me (mono-, di-, tri-, tetra-), Et, nPro, nBu, and iBu substituents.)

TABLE 2-continued
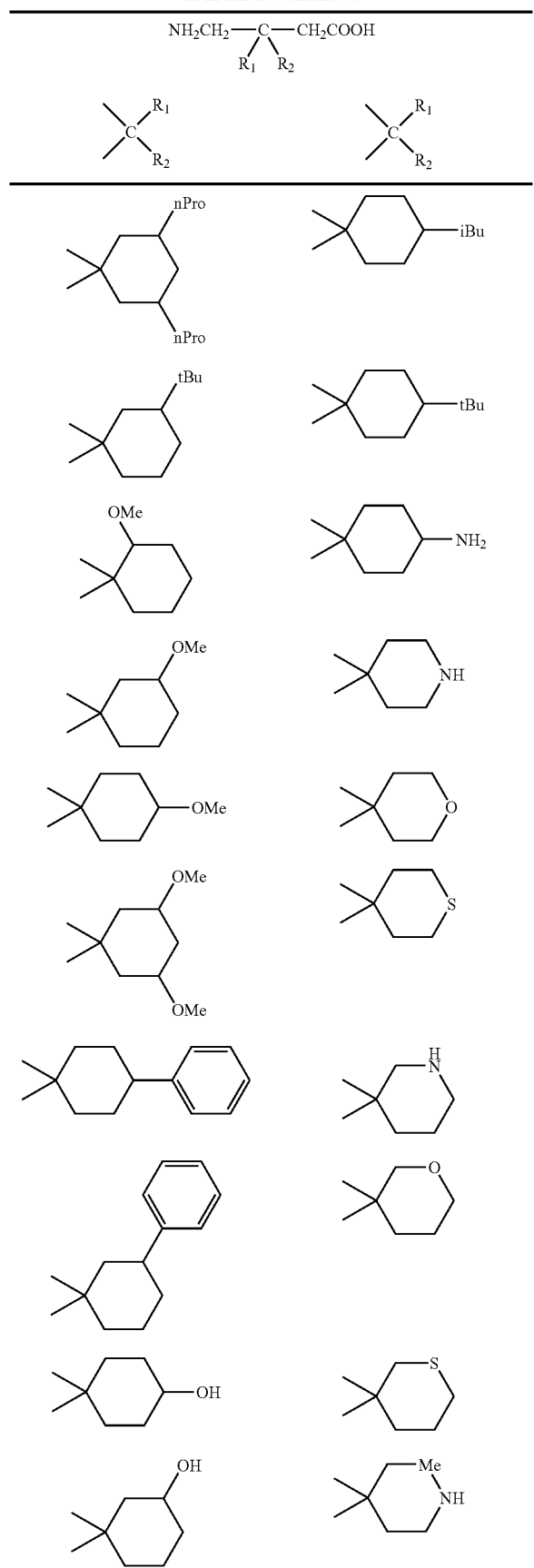
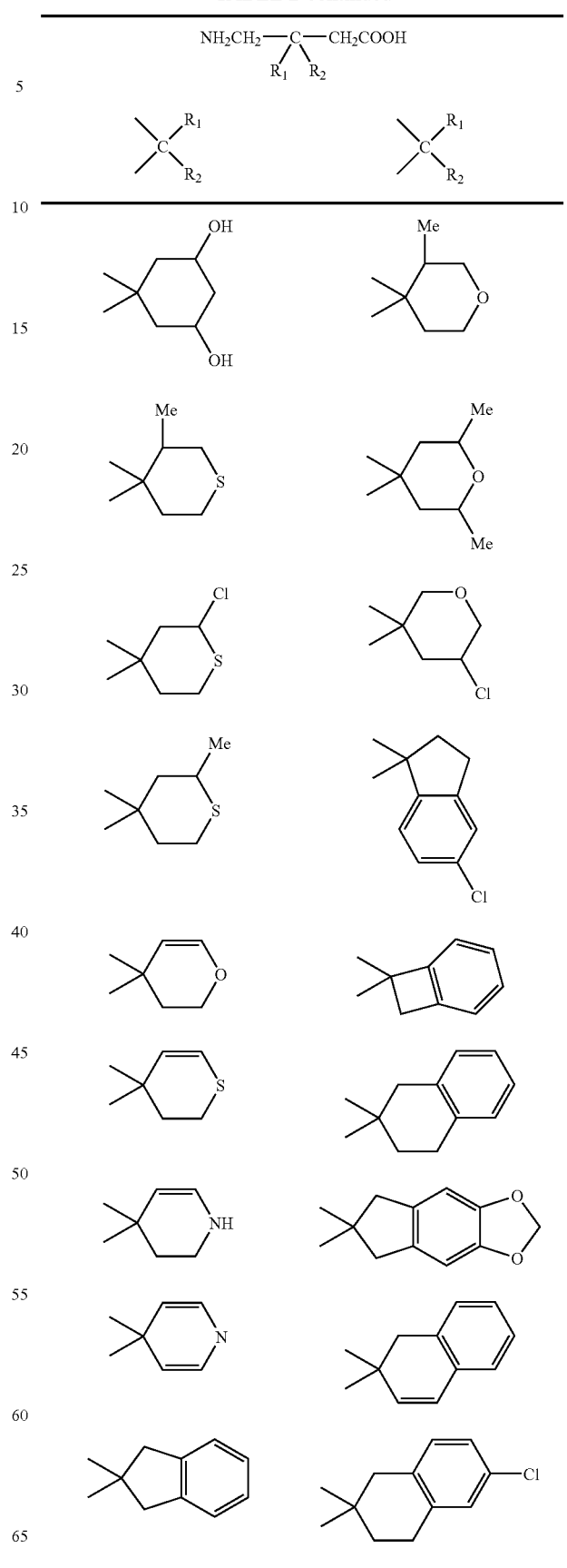

TABLE 2-continued

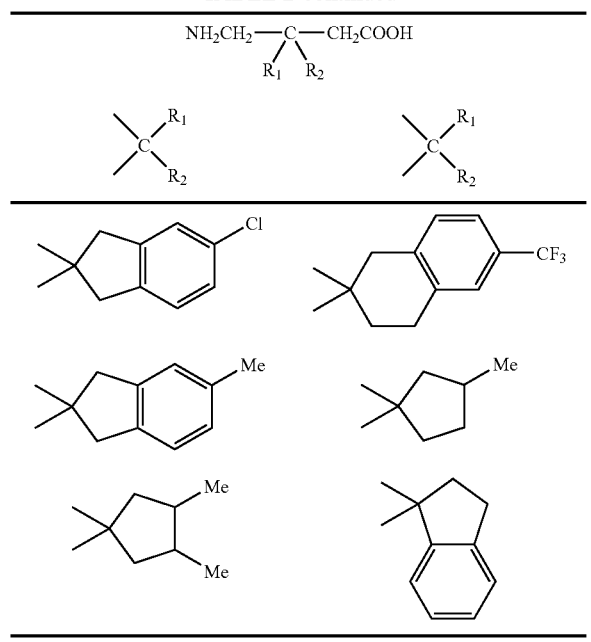

The present invention provides an extremely effective stabilizing means in manufacturing a pharmaceutical preparation containing a 4-amino-3-substituted-butanoic acid derivative having a bulky substituent at the 3-position thereof as explained above, and the means of the invention is extremely effective in preparing a pharmaceutical preparation of, for example, gabapentin, pregabalin, baclofen, 3-aminomethyl-4-cyclohexyl-butanoic acid, 3-aminomethyl-5-cyclohexyl-pentanoic acid, 3-aminomethyl-4-phenyl-butanoic acid, 3-aminomethyl-5-phenyl-pentanoic acid, etc.

The humectant which may be employed in the invention in combination with a 4-amino-3-substituted-butanoic acid derivative is selected from ethylene glycol, propylene glycol, butylene glycol, sorbitol and glycerol and an aliphatic acid ester thereof, alone or in any combination of two or more thereof.

Illustrative examples of the glycerol aliphatic acid esters may include glycerol lower aliphatic acid esters such as monoacetylglyceride, diacetylglyceride, triacetylglyceride (triacetin), middle chain aliphatic acid monoglyceride such as monohexanoylglyceride, monooctanoylglyceride, monodecanoylglyceride, and middle chain aliphatic acid polyglycerol ester such as monolauric acid polyglyceride or monomyristic acid polyglyceride and the like.

The solid pharmaceutical preparation of the present invention can be obtained in a usual dosage form, typically, in the dosage form of powders, granules, surface-coated granules, capsules, tablets or surface-coated tablets by conducting in turn the granulation step in which a humectant as a stabilizer and, if necessary, an auxiliary agent for manufacturing a pharmaceutical preparation are added to bulk powders of a 4-amino-3-substituted-butanoic acid derivative, such as gabapentin, pregabalin, baclofen and the like and the resulting mixture is granulated by means of a granulator, the encapsulation step in which the resulting granular powders are encapsulated under compression by means of a capsule filler or the tableting step in which the resulting granular powders are compressed by means of a tablet machine and, if necessary, the coating step in which the granular powders, tablets or granules obtained in the preceding steps are surface-coated.

The granulation of the 4-amino-3-substituted-butanoic acid derivative during the process for manufacturing pharmaceutical preparations as stated above such as gabapentin may be conducted by any granulation method well-known per se, for example, a fluidized granulation method, a high speed stirring granulation method, a melting granulation method and the like. In order to effectively adhere a stabilizer to bulk powders of the 4-amino-3-substituted-butanoic acid derivative, there may be preferably employed a fluidized granulation method in which bulk powders of the said compound are fluidized and then a stabilizer is sprayed onto the fluidized powders. In this fluidized granulation step, a stabilizer is added in the form of its solution dissolved in water or an organic solvent such as alcohols or the like, whereby a small amount of the stabilizer may be sufficient for uniformly adhering to the surface of bulk powders of the 4-amino-3-substituted butanoic acid derivative.

In the granulation step using said fluidized granulation method, granulation may be carried out by adding to bulk powders of the 4-amino-3-substituted-butanoic acid derivative the stabilizer solution as described above and, if necessary, a binder such as corn starch, a cellulose derivative (eg, hydroxypropylcellulose), polyvinyl alcohol, a polyvinyl pyrrolidone (eg, Kollidon-K30 or Kollidon-K25), a copolyvidone (eg, Kollidon-VA64) and the like in the form of a solution or suspension thereof.

The aforementioned stabilizer solution may be applied to bulk powders of the 4-amino-3-substituted-butanoic acid derivative prior to the granulation using the binder or other auxiliaries for manufacturing a pharmaceutical preparation. In this granulation step, there may be also incorporated, if necessary, a sweetening agent such as mannitol, sorbitol, xylitol or the like and other auxiliaries for manufacturing a pharmaceutical preparation.

The granular powders thus obtained may be used as a pharmaceutical preparation of the 4-amino-3-substituted-butanoic acid derivative as such, or they may be also encapsulated under compression for capsules containing the 4-amino-3-substituted-butanoic acid derivative. Also, they may be further compressed to tablets.

More specifically, the granular powders of the 4-amino-3-substituted-butanoic acid derivative obtained as described above can be compression-molded to tablets by means of a tablet machine. It is essential in this compression-molding step to use a lubricant as ordinarily done for the manufacture of a pharmaceutical preparation. However, it has been discovered that some conventional lubricants employed in a compression-molding step for drugs may influence on a stability with lapse of time of the pharmaceutical preparations of the 4-amino-3-substituted-butanoic acid derivative and further bring about a delayed dissolution of the drugs, so that these lubricants are not preferable in some cases.

However, we have also found out that a certain neutral amino acid, which have hardly been used as a lubricant in compressing drugs, such as L-leucine, L-isoleucine, L-valine, D-leucine, D-isoleucine, D-valine, DL-leucine, DL-isoleucine or DL-valine or a mixture thereof can exert a remarkable effect as a lubricant for compression-molding into tablets of the present derivative such as gabapentin and that in the tablets thus prepared, there has been no adverse influence on both the stability with lapse of time and dissolution property provided by the present stabilizer.

Thus, in this compression-molding step, the resulting granules may be usually blended with L-leucine, L-isoleucine, L-valine, D-leucine, D-isoleucine, D-valine, DL-leucine, DL-isoleucine, DL-valine or a mixture thereof as a lubricant and, if necessary, an auxiliary for manufacturing a pharmaceutical preparation, for example, a binder or a disintegrator such as a cellulose derivative (eg, hydroxypropylcellulose), crystalline cellulose, corn starch, partially gelatinized starch, lactose or the like or other conventional auxiliaries by means of a suitable mixer such as a dry mixer, eg, a V-blender or the like and then the resulting mixture is compression-molded to tablets by means of a suitable tablet machine.

The granular powders, granules or tablets thus obtained may be surface-coated, if necessary. The surface-coating step for tablets is not essential and may be an optional step. For example, in case of gabapentin having a strongly bitter taste, it may be desirable to surface-coat gabapentin tablets for easier ingestion. In the surface-coating step, there may be used as a film-forming material a polymeric base ingredient such as a cellulose derivative, eg, hydroxypropylcellulose (HPC), hydroxypropylmethyl-cellulose (HPMC), etc., a polyvinyl pyrrolidone, Kollidon-VA64, Eudragits, etc., and as a sweetening agent mannitol, sorbitol, xylitol, aspartame and the like.

To such a film-forming material, there may be further added, if necessary, a humectant such as propylene glycol, glycerol, triacetin or the like and a neutral amino acid such as L-leucine, L-isoleucine, L-valine, L-alanine, D-leucine, D-isoleucine, D-valine, D-alanine, DL-leucine, DL-isoleucine, DL-valine, DL-alanine or glycine. Among those compounds, propylene glycol, glycerol and triacetin may exhibit not only an activity as a humectant but also an activity as a plasticizer for a coating film, while L-leucine, L-isoleucine, L-valine, D-leucine, D-isoleucine, D-valine, DL-leucine, DL-isoleucine and DL-valine may exhibit an activity as a modifier for a coating film. Moreover, when the 4-amino-3-substituted-butanoic acid derivative is gabapentin, glycine, L-alanine, D-alanine and DL-alanine may exhibit an activity as a buffering agent against bitter taste of gabapentin. The surface-coating of the granular powders, granules or tablets may be applied to the surface of the granular powders, granules or tablets according to a well-known method using a fluidized bed or a rotary pan.

In a solid composition containing the 4-amino-3-substituted-butanoic acid derivative according to this invention, the humectant may be used in a total amount of 0.01-25% by weight relative to the 4-amino-3-substituted-butanoic acid derivative, or in an amount of 0.01-25% by weight relative to the total amount of the 4-amino-3-substituted-butanoic acid derivative and the auxiliary agent when added for manufacturing a pharmaceutical preparation. The total amount to be used may be varied depending upon the sort of the humectant to be used, the specific dosage form of the solid composition containing the 4-amino-3-substituted-butanoic acid derivative, in other words, tablets, powders, granules or capsules, and also the sort and amount of an auxiliary to be added. The humectant should be used, in any case, in an effective amount to stabilize the 4-amino-3-substituted-butanoic acid derivative by ensuring a water retention of the pharmaceutical preparation. And, in many cases, a total amount of the humectant may be preferably in the range of 0.02-20% by weight relative to the 4-amino-3-substituted-butanoic acid derivative, or it may preferably be in the range of 0.02-20% by weight relative to the total amount of the 4-amino-3-substituted-butanoic acid derivative and an auxiliary agent when added for manufacturing a pharmaceutical preparation. However, when sorbitol is used together with other humectants, the amount to be used is not limited to the ranges as mentioned above.

In preparing surface-coated tablets of the 4-amino-3-substituted-butanoic acid derivative, the amount of the humectant to be used in the surface-coating step may be usually in the range of 0.1-50% by weight relative to the total amount of the coating materials.

Moreover, we have also found out that in preparing a solid pharmaceutical preparation of the 4-amino-3-substituted-butanoic acid derivative, use of a certain neutral amino acid including L-leucine, L-isoleucine, L-valine, L-alanine, D-leucine, D-isoleucine, D-valine, D-alanine, DL-leucine, DL-isoleucine, DL-valine, DL-alanine and glycine, instead of the auxiliary agent commonly used for manufacturing a pharmaceutical preparation, can bring about the desired pharmaceutical preparation without any prevention of the water retention effect of a humectant as a stabilizer of this invention. In other words, the said neutral amino acid may exhibit an activity as auxiliaries for stabilization. The said neutral amino acid may be used alone or in combination of two or more thereof. The said neutral amino acid may be blended in any optional step for the preparation of a pharmaceutical preparation of the 4-amino-3-substituted-butanoic acid derivative including the granulation step. A total amount of the said neutral amino acid to be used, for example, in a gabapentin solid preparation is in the range of 0.05-40% by weight relative to gabapentin.

The process for preparing a solid preparation of the 4-amino-3-substituted-butanoic acid derivative according to the invention as explained above comprises, for example, the granulation step in which a humectant, that is, a stabilizer, a binder and an auxiliary agent for manufacturing a pharmaceutical preparation are added to bulk powders of the said compound and then the resulting mixture is granulated by means of a granulator, the step for tableting in which additives such as a lubricant are added to the resulting granular powders and then the granules are compressed by means of a tableting machine and, if necessary, the coating step in which the surface of tablets obtained is coated. However, the granular powders as prepared by the granulation step may be applied as such in the dosage form of powders or granules as a pharmaceutical preparation of the 4-amino-3-substituted-butanoic acid derivative without conducting the tableting step, or the granules as prepared by the granulation step may be further subjected to the surface-coating step as described above. Alternatively, the granules as prepared by the granulation step may be admixed with a lubricant or the like and the resulting mixture may be filled into gelatin hard capsules by means of a capsule filler to prepare capsules. In the solid preparation of the 4-amino-3-substituted-butanoic acid derivative thus prepared, for example, in case of the gabapentin preparation, gabapentin is in a compressed or fluidized state so that the solid preparation may be easily taken when orally administered to human.

This invention will be more fully explained by way of the following examples, but it should not be construed that these examples limit the scope of this invention.

EXAMPLE 1

1) Preparation of Granular Powders A of Gabapentin

On 250 g of bulk powders of gabapentin was sprayed 72 g of water by means of a fluidized granulator (manufactured by FREUND Co., Ltd., SFC-Labo) and then dried to obtain gabapentin granular powders A.

2) Preparation of Granular Powders B of Gabapentin

On 250 g of bulk powders of gabapentin was sprayed a solution of 5 g of propylene glycol in 67 g of water by means of said fluidized granulator and then dried to obtain gabapentin granular powders B.

The gabapentin granular powders A and B obtained as described in the above 1) and 2) were stored under the conditions as defined in the following Table 3 and then a lactam content formed in each of the granular powders was determined by means of HPLC.

The lactam content in this example and examples hereinafter is expressed in term of % by weight based on gabapentin.

TABLE 3

| Storage conditions | Granular Powders | |
|---|---|---|
| | A | B |
| When initiated | 0.003 | 0.003 |
| 60° C./1 week (sealed) | 0.017 | 0.011 |
| 60°/2 weeks (sealed) | 0.020 | 0.013 |
| 50° C./85% humidity/2 weeks (open) | 0.003 | 0.003 |
| 50° C./85% humidity/4 weeks (open) | 0.003 | 0.003 |

The above table shows that the gabapentin bulk powders could be prevented from the degradation with lapse of time (the lactam formation) by the addition of propylene glycol.

EXAMPLE 2

1) Preparation of Granular Powders C of Gabapentin

On 250 g of bulk powders of gabapentin was sprayed 72 g of water by means of a fluidized granulator (manufactured by FREUND Co., Ltd., SFC-Labo) and subsequently a solution of 5 g of hydroxypropylcellulose in 58 g of water was sprayed thereon, and then dried to obtain gabapentin granular powders C.

2) Preparation of Granular Powders D of Gabapentin

On 250 g of bulk powders of gabapentin was sprayed a solution of 5 g of propylene glycol in 67 g of water by means of a fluidized granulator (manufactured by FREUND Co., Ltd., SFC-Labo) and subsequently a solution of 5 g of hydroxypropylcellulose in 58 g of water was sprayed thereon, and then dried to obtain gabapentin granular powders D.

3) Preparation of Granular Powders E of Gabapentin

On 250 g of bulk powders of gabapentin was sprayed a solution of 5 g of triacetin in 67 g of water by means of said fluidized granulator and subsequently a solution of 5 g of hydroxypropylcellulose in 58 g of water was sprayed thereon, and then dried to obtain gabapentin granular powders E.

4) Preparation of Granular Powders F of Gabapentin

On 250 g of bulk powders of gabapentin was sprayed a solution of 2.5 g of propylene glycol and 2.5 g of triacetin in 67 g of water by means of the said fluidized granulator and subsequently a solution of 5 g of hydroxypropylcellulose in 58 g of water was sprayed thereon, and then dried to obtain gabapentin granular powders F.

The gabapentin granular powders C-F obtained as described in the above 1) through 4) were stored under the conditions as defined in the following Table 4 and then a lactam content formed in each of the granular powders was determined by means of HPLC.

TABLE 4

| Storage Conditions | Granular Powders | | | |
|---|---|---|---|---|
| | C | D | E | F |
| When initiated | 0.004 | 0.003 | 0.003 | 0.003 |
| 60° C./1 week (sealed) | 0.131 | 0.076 | 0.044 | 0.072 |
| 60° C./2 weeks (sealed) | 0.214 | 0.130 | 0.118 | 0.124 |
| 50° C./85% humidity/2 weeks (open) | 0.011 | 0.008 | 0.006 | 0.007 |
| 50° C./85% humidity/4 weeks (open) | 0.012 | 0.013 | 0.010 | 0.011 |

The above table shows that the gabapentin bulk powders could be prevented from the degradation with lapse of time (the lactam formation) by the addition of either propylene glycol or triacetin or both of them.

EXAMPLE 3

1) Preparation of Gabapentin Granules

On 700 g of bulk powders of gabapentin was sprayed a solution of 14 g of copolyvidone and 14 g of propylene glycol in 252 g of water by means of a fluidized granulator (manufactured by FREUND Co., Ltd., SFC-Mini) and then dried to obtain gabapentin granular powders.

2) Compression to Tablets

The dry granules obtained according to the above step 1) were admixed with L-valine at 7% by weight based on the granules and then compressed to tablets, each tablet having a diameter of 9 mm and a weight of 336 mg, by means of a rotary tablet machine (manufactured by KIKUSUI SEI-SAKUSHO K.K.). Each tablet contained 300 mg of gabapentin and had a hardness of 6-10 kg.

3) Surface Coating of Tablets

Tablets obtained in the above step 2) were film coated over the surface thereof with a coating solution having the composition as defined in the following Table 5 by means of a coater (manufactured by FREUND Co., Ltd., HI-COATOR HCT-30).

TABLE 5

| Copolyvidone | 34.0 g |
|---|---|
| L-Isoleucine | 13.5 g |
| Glycine | 13.5 g |
| Propylene glycol | 7.0 g |
| Calcium stearate | 7.0 g |
| Water | 432.0 g |

The uncoated tablets (I) and the film-coated tablets (II) obtained according to the above steps 2) and 3) and the commercially available gabapentin capsules (III) were stored under the conditions as defined in the following Table 6 and thereafter a content of the lactam as formed in each of the said tablets and capsules were determined.

TABLE 6

| | Lactam Content (%) Gabapentin Preparations | | |
|---|---|---|---|
| Storage Conditions | (I) | (II) | (III)* |
| When initiated | 0.005 | 0.004 | 0.018 |
| 40° C./75% humidity/2 months (sealed) | 0.048 | 0.066 | 0.072 |
| 40° C./75% humidity/4 months (sealed) | 0.123 | 0.119 | 0.129 |
| 40° C./75% humidity/6 months (sealed) | 0.229 | 0.172 | 0.219 |

[Note]
*commercially available gabapentin capsules prepared according to a dry blend method, each capsule containing 300 mg of gabapentin The above table shows that no significant increase in the lactam content was observed in the film coated tablets and the film coated tablets had an excellent stability with lapse of time, similar to that of the gabapentin capsules prepared by a dry blend method.

Moreover, the film coated tablets obtained as described above were subjected to the dissolution test according to the dissolution test procedure as prescribed in the Japanese Pharmacopoeia XIII (using 900 mL of water and a puddle method at 50 rpm). The test conditions and test results are shown in the following Table 7 wherein the numerical value means to represent the dissolution amount expressed in terms of %.

TABLE 7

| Dissolution time (min.) | Storage Conditions | |
|---|---|---|
| | When Initiated | 60° C./4 hrs (sealed) |
| 15 | 90.3 | 91.5 |
| 30 | 103.1 | 103.3 |
| 60 | 103.2 | 103.3 |

The above test results have proved that the film coated gabapentin tablets prepared according to the process of this invention can exhibit a good dissolution in the dissolution test and also have a good stability with lapse of time after dissolution.

EXAMPLE 4

1) Preparation of Baclofen Powder Sample G 200 mg of baclofen crystals was wetted with 0.04 mL of water and the mixture was made to granular powders by means of a mortar and then dried to obtain baclofen powder sample G.

2) Preparation of Baclofen Powder Sample H 200 mg of baclofen crystals was wetted with 0.04 mL of a 20% aqueous solution of propylene glycol and the mixture was made to granular powders by means of a mortar and then dried to obtain baclofen powder sample H.

The baclofen powder samples G and H obtained as described above and untreated baclofen crystals were stored under the conditions as defined in the following Table 8 and then a content of dehydrated condensates formed in each of the samples was determined by means of HPLC. In this Example, the content of the dehydrated condensates is expressed in terms of % by weight, based on baclofen.

TABLE 8

| | Samples | | |
|---|---|---|---|
| Storage Conditions | Untreated Baclofen | G | H |
| When Initiated | 0.10 | 0.10 | 0.10 |
| 60° C./1 week (sealed) | 0.36 | 0.95 | 0.42 |
| 60° C./2 weeks (sealed) | 0.57 | 1.26 | 0.61 |
| 60° C./3 weeks (sealed) | 0.70 | 1.54 | 0.82 |

The above table shows that the granulated baclofen using water underwent an accelerated degradation with lapse of time (condensation with dehydration), and that the degradation with lapse of time could be prevented by the addition of propylene glycol as a humectant.

EXAMPLE 5

1) Preparation of Pregabalin Powder Sample I

One gram of pregabalin crystals was wetted with 0.1 mL of water and the mixture was made to granular powders by means of a mortar and then dried to obtain pregabalin powder sample I.

2) Preparation of Pregabalin Powder Sample J

One gram of pregabalin crystals was wetted with 0.1 mL of a 1% aqueous solution of decaglyceryl monolaurate and the mixture was made to granular powders by means of a mortar and then dried to obtain pregabarin powder sample J.

3) Preparation of Pregabalin Powder Sample K

One gram of pregabalin crystals was wetted with 0.1 mL of a 10% aqueous solution of butylene glycol and the mixture was made to granular powders by means of a mortar and then dried to obtain pregabalin powder sample K.

The samples I, J and K obtained as described above and untreated pregabalin crystals were stored under the conditions as defined in the following Table 9 and then a content of the dehydrated condensate formed in each of the samples was determined by means of HPLC. In the present Example and the following Example 6, a content of the dehydrated condensate is expressed in terms of % by weight, based on pregabalin.

TABLE 9

| | Samples | | | |
|---|---|---|---|---|
| Storage Conditions | Untreated Pregabalin | I | J | K |
| When initiated | <0.001 | <0.001 | <0.001 | <0.001 |
| 60° C./1 week (sealed) | 0.001 | 0.009 | 0.001 | 0.001 |
| 60° C./2 weeks (sealed) | 0.001 | 0.010 | 0.002 | 0.002 |

The above table shows that the granulated pregabalin using water underwent an accelerated degradation with lapse of time (condensation with dehydration) and that the degradation with lapse of time could be prevented by the addition of decaglyceryl monolaurate or butylene glycol as a humectant.

EXAMPLE 6

1) Preparation of Pregabalin Powder Sample L

One gram of pregabalin crystals was wetted with 0.1 mL of a 10% aqueous solution of hydroxypropylcellulose and the mixture was made to granular powders by means of a mortar and then dried to obtain pregabalin powder sample L.

2) Preparation of Pregabalin Powder Sample M

One gram of pregabalin crystals was wetted with 0.1 mL of an aqueous solution containing 10% hydroxypropylcellulose and 10% propylene glycol, and the mixture was made to granular powders by means of a mortar and then dried to obtain pregabalin powder sample M.

The samples L and M obtained as described above were stored under the conditions as defined in the following Table 10 and then a content of the dehydrated condensate formed in each of the samples was determined by means of HPLC.

TABLE 10

| | Samples | |
|---|---|---|
| Storage Conditions | L | M |
| When initiated | <0.001 | <0.001 |
| 60° C./1 week (sealed) | 0.005 | 0.001 |
| 60° C./2 weeks (sealed) | 0.010 | 0.002 |
| 60° C./4 weeks (sealed) | 0.014 | 0.004 |

The above table shows that the degradation with lapse of time (condensation with dehydration) of the pregabalin could be prevented by the addition of hydroxypropylcellulose and propylene glycol as a humectant.

It has been believed that an excess water remaining generally in solid preparations including a preparation of the 4-amino-3-substituted-butanoic acid derivative would be undesirable since it may cause discoloration, degradation, tableting troubles or the like. It is the most significant feature of this invention that, unexpectedly, a stability of a solid preparation of the 4-amino-3-substituted-butanoic acid derivative can be remarkably improved by the addition of a humectant which has a water retention activity and has been considered to trigger unfavorable disturbances in the said preparation as stated above. Thus, the present invention has now provided a means for stabilizing pharmaceutically unstable 4-amino-3-substituted-butanoic acid derivatives including gabapentin, and further elucidated the principle of this stabilization, which have been regarded as the problems to be solved in the art over many years. A significant effect of this invention is that the wet granulation method using water, which has been widely utilized for a small-sized pharmaceutical preparation to be easily taken by patients, can be applied to gabapentin having an extremely poor moldability without causing any degradation of gabapentin. The present invention can be expected to greatly contribute to the development of a stabilized pharmaceutical composition containing the 4-amino-3-substituted-butanoic acid derivative.

What is claimed is:

1. A tablet which comprises:
   a) crystalline pregabalin,
   b) a humectant selected from the group consisting of ethylene glycol, propylene glycol, butylene glycol, sorbitol, glycerol and an aliphatic acid ester of glycerol,
   c) optionally, an auxiliary agent for manufacturing said tablet, and;
   d) a residual amount of water, wherein said amount of water is sufficient to stabilize said crystalline pregabalin.

2. The tablet according to claim 1 in which said humectant is propylene glycol.

3. The tablet according to claim 1 wherein the total amount of said humectant is from 0.01-25% by weight relative to said pregabalin.

4. The tablet according to claim 1 wherein the total amount of said humectant is from 0.01-25% by weight relative to said pregabalin and said auxiliary agent.

5. A process for the preparation of the pregabalin-containing tablet according to claim 1 which comprises combining the crystalline pregabalin with the humectant selected from the group consisting of ethylene glycol, propylene glycol, butylene glycol, sorbitol, glycerol and an aliphatic acid ester of glycerol and, optionally, the auxiliary agent for manufacturing said tablet.

6. The process according to claim 5 in which said humectant is propylene glycol.

7. The tablet according to claim 1 further comprising a neutral amino acid.

8. The tablet according to claim 1 further comprising a neutral amino acid selected from the group consisting of L-leucine, L-isoleucine, L-valine, L-alanine, D-leucine, D-isoleucine, D-valine, D-lanine, DL-leucine, DL-isoleucine, DL-valine, DL-alanine, and glycine.

9. The tablet according to claim 7 in which said neutral amino acid is leucine.

* * * * *